United States Patent [19]
Lattin et al.

[11] Patent Number: 5,879,322
[45] Date of Patent: Mar. 9, 1999

[54] SELF-CONTAINED TRANSDERMAL DRUG DELIVERY DEVICE

[75] Inventors: Gary A. Lattin, Forest Lake; Tighe M. Belden, Minneapolis, both of Minn.; Andrew J. Withell, Auckland, New Zealand

[73] Assignee: ALZA Corporation, Palo Alto, Calif.

[21] Appl. No.: 410,203

[22] Filed: Mar. 24, 1995

[51] Int. Cl.⁶ .................................................. A61N 1/30
[52] U.S. Cl. ............................................. 604/20; 607/152
[58] Field of Search ............................. 604/20; 607/115, 607/149, 152

[56] References Cited

U.S. PATENT DOCUMENTS

| | | |
|---|---|---|
| 351,233 | 10/1886 | Watkins . |
| 385,556 | 7/1888 | Hoke . |
| 486,902 | 11/1892 | Shults . |
| 770,014 | 9/1904 | Linn . |
| 857,664 | 6/1907 | Overman . |
| 2,301,567 | 11/1942 | Morse . |
| 2,667,162 | 1/1954 | Zwahlen . |
| 2,784,715 | 3/1957 | Kestler . |
| 4,141,359 | 2/1979 | Jacobsen et al. . |
| 4,166,457 | 9/1979 | Jacobsen et al. . |
| 4,474,570 | 10/1984 | Ariura et al. . |
| 4,588,580 | 5/1986 | Gale et al. . |
| 4,708,716 | 11/1987 | Sibalis . |
| 4,725,263 | 2/1988 | McNichols et al. ....................... 604/20 |
| 4,911,688 | 3/1990 | Jones . |
| 4,997,418 | 3/1991 | DeMartini . |
| 5,006,108 | 4/1991 | LaPrade . |
| 5,037,381 | 8/1991 | Bock et al. . |
| 5,047,007 | 9/1991 | McNichols et al. . |
| 5,053,001 | 10/1991 | Reller et al. . |
| 5,135,479 | 8/1992 | Sibalis et al. . |
| 5,135,480 | 8/1992 | Bannon et al. . |
| 5,195,953 | 3/1993 | DeMartini . |
| 5,203,768 | 4/1993 | Haak et al. . |
| 5,224,927 | 7/1993 | Tapper . |
| 5,224,928 | 7/1993 | Sibalis et al. . |
| 5,246,418 | 9/1993 | Haynes et al. . |
| 5,254,081 | 10/1993 | Maurer et al. . |
| 5,358,483 | 10/1994 | Sibalis ....................................... 604/20 |
| 5,458,569 | 10/1995 | Kirk, III et al. . |
| 5,498,235 | 3/1996 | Flower . |

FOREIGN PATENT DOCUMENTS

| | | | |
|---|---|---|---|
| 0337642 | 10/1989 | European Pat. Off. ......... A61N 1/30 |
| 0642808 | 3/1995 | European Pat. Off. ......... A61N 1/30 |
| 2239803 | 7/1991 | United Kingdom ............. A61N 1/30 |
| 9115261 | 10/1991 | WIPO ....................................... 604/20 |
| WO9415669 | 7/1994 | WIPO ................................. A61N 1/30 |
| WO9428965 | 12/1994 | WIPO ........................... A61M 37/00 |

*Primary Examiner*—Mark Bockelman
*Attorney, Agent, or Firm*—D. Byron Miller; Steven F. Stone

[57] ABSTRACT

A method for manufacturing a transdermal drug delivery device (10) is disclosed wherein a component (32) and/or a subassembly (20) are intentionally adapted to be separable from the rest of the device for disposal which is more medically or environmentally acceptable. In one embodiment, device 10 comprises upper and lower housings (16, 20), with lower housing (20) being separable from upper housing (16) and foldable upon itself to minimize medically unacceptable contact with, e.g., a drug reservoir (26 or 28) contained therein. A device (10) made in accordance with the invention is included.

19 Claims, 4 Drawing Sheets

SELF-CONTAINED TRANSDERMAL DRUG DELIVERY DEVICE

TECHNICAL FIELD

The present invention relates to delivery of drug or agent transdermally. More specifically, the present invention relates to delivery of drug or agent transdermally by electrotransport means utilizing self-contained electrotransport devices. Yet more specifically, the present invention relates to methods and apparatus for transdermal delivery of drug or agent in which apparatus components or subcomponents are intentionally designed to be separable therefrom so as to enhance the environmental or medical acceptability of the apparatus, the separable component or subcomponent, or both.

BACKGROUND ART

Recently, much attention in the patent and technical literature has been directed to delivery of drug or agent through intact skin or organ surfaces by either passive processes, e.g., diffusion, or active processes, e.g., electrotransport. The present invention relates to both such transdermal processes, but will be here described with primary reference to active transdermal processes. The term "electrotransport" as used herein refers generally to the delivery of a beneficial agent (e.g., a drug) through a biological membrane, such as skin, mucous membrane, or nails. The delivery is induced or aided by application of an electrical potential. For example, a beneficial therapeutic agent may be introduced into the systemic circulation of a human body by electrotransport delivery through the skin. A widely used electrotransport process, electromigration (also called iontophoresis), involves the electrically induced transport of charged ions. Another type of electrotransport, electroosmosis, involves the flow of a liquid under the influence of an electric field, the liquid containing the agent to be delivered. Still another type of electrotransport process, electroporation, involves the formation of transiently-existing pores in a biological membrane by the application of an electric field. An agent can be delivered through the pores either passively (i.e., without electrical assistance) or actively (i.e., under the influence of an electric potential). However, in any given electrotransport process, more than one of these processes may be simultaneously occurring.

Accordingly, the term "electrotransport", as used herein, should be given its broadest possible interpretation so that it includes the electrically induced or enhanced transport of at least one agent, which may be charged, uncharged, or a mixture of charged and uncharged species, regardless of the specific mechanism or mechanisms by which the agent actually is transported.

Electrotransport devices use at least two electrodes that are in electrical contact with some portion of the skin, nails, mucous membrane, organ surfaces, or other surface of the body. One electrode, commonly called the "donor" or "active" electrode, is the electrode from which the agent is delivered into the body. The other electrode, typically termed the "counter" or "return" electrode, serves to close the electrical circuit through the body. For example, if the agent to be delivered is positively charged, i.e., a cation, then the anode is the active or donor electrode, while the cathode serves to complete the circuit. Alternatively, if an agent is negatively charged, i.e., an anion, the cathode is the donor electrode. Additionally, both the anode and cathode may be considered donor electrodes if both anionic and cationic agent ions, or if uncharged dissolved agents, are to be delivered.

Furthermore, electrotransport delivery systems generally require at least one reservoir or source of the agent to be delivered to the body. Examples of such donor reservoirs include a pouch or cavity, a porous sponge or pad, and a hydrophilic polymer or a gel matrix. Such donor reservoirs are electrically connected to, and positioned between, the anode electrode or cathode electrode (depending upon the agent) and the body surface, to provide a fixed or renewable source of one or more agents or drugs. Electrotransport devices also have an electrical power source such as one or more batteries. Typically, one pole of the power source is electrically connected to the donor electrode, while the opposite pole is electrically connected to the counter electrode. In addition, some electrotransport devices have an electrical controller that controls the current applied through the electrodes, thereby regulating the rate of agent delivery. Furthermore, passive flux control membranes, adhesives for maintaining device contact with a body surface, insulating members, and impermeable backing members are some other potential components of an electrotransport device.

All electrotransport agent delivery devices utilize an electrical circuit to connect electrically the power source (e.g., a battery) and the electrodes. In very simple devices, such as those disclosed in Ariura et al. U.S. Pat. No. 4,474,570, the "circuit" is merely an electrically conductive wire used to connect the battery to an electrode. Other devices use a variety of electrical components to control the amplitude, polarity, timing, waveform shape, etc. of the electric current supplied by the power source. See, for example, McNichols et al. U.S. Pat. No. 5,047,007.

To date, commercial transdermal electrotransport drug delivery devices (e.g., the Phoresor, sold by Iomed, Inc. of Salt Lake City, Utah; the Dupel Iontophoresis System sold by Empi, Inc. of St. Paul, Minn.; the Webster Sweat Inducer, model 3600, sold by Wescor, Inc. of Logan, Utah) have generally utilized a desk-top electrical power supply unit and a pair of skin contacting electrodes. The donor electrode reservoir contains a drug solution while the counter electrode reservoir contains a solution of a bio-compatible electrolyte salt. The "satellite" electrodes are connected to the electrical power supply unit by long (e.g., 1–2 meters) electrically conductive wires or cables. Examples of desk-top electrical power supply units which use "satellite" electrode assemblies are disclosed in Jacobsen et al. U.S. Pat. No. 4,141,359 (see FIGS. 3 and 4); LaPrade U.S. Pat. No. 5,006,108 (see FIG. 9); and Maurer et al. U.S. Pat. No. 5,254,081 (see FIGS. 1 and 2).

More recently, small, self-contained electrotransport delivery devices or assemblies, adapted to be worn on the skin for extended periods of time, have been proposed. The electrical components of such miniaturized electrotransport drug delivery devices are also preferably miniaturized, and may be in the form of either integrated circuits (i.e., microchips) or small printed circuits. Electronic components, such as batteries, resistors, pulse generators, capacitors, etc., are electrically connected to form an electronic circuit that controls the amplitude, polarity, timing, waveform shape (and other parameters) of the electric current supplied by the power source. Such small self-contained electrotransport delivery devices are disclosed, for example, in Tapper U.S. Pat. No. 5,224,927; Haak et al. U.S. Pat. No. 5,203,768; Sibalis et al. U.S. Pat. No. 5,224,928; and Haynes et al. U.S. Pat. No. 5,246,418.

In contrast with electrotransport transdermal devices, passive transdermal devices are generally much simpler. For example, Gale et al. U.S. Pat. No. 4,588,580 discloses a transdermal drug delivery device which delivers a therapeutic amount of a drug, e.g., fentanyl, by passive diffusion through intact skin. As is described in the Gale et al. '580 patent, a passive transdermal therapeutic system comprises a pouch formed from a drug/solvent/gel impermeable backing, a drug elution rate-controlling membrane which, with the pouch, forms a drug reservoir. The drug reservoir contains a dissolved or suspended drug therein. The entire assembly is held in place on a patient's skin by a biocompatible adhesive layer located on the skin-contacting side of the device.

One drawback with small (i.e., wearable) unitary electrotransport systems which are manufactured with a predetermined amount of drug in the device, is that once the drug is depleted, the entire device must be discarded. Such integrated devices, of necessity, have components or subassemblies, e.g., batteries, drug reservoirs and electrical subassemblies, all of which are simultaneously discarded into the environment at the time of device disposal. Further, transdermal electrotransport delivery of extremely potent drugs such as narcotic analgesics, which are potentially addictive, can have serious side effects, e.g., respiratory depression. Thus, availability of safe (or even regulated) disposal of drug-containing components or subcomponents of self-contained, wearable, transdermal (especially electrotransport) devices will permit such devices to become more commercially acceptable.

DISCLOSURE OF THE INVENTION

It is an aspect of the present invention to provide a transdermal drug delivery device with minimal adverse environmental or medical impact upon disposal.

It is another aspect of the present invention to provide a transdermal drug delivery device intentionally having separable subcomponents or subassemblies.

In one aspect, the present invention is a self-contained, internally-powered electrotransport drug delivery device (e.g., to deliver narcotic analgesics) having removable or replaceable subcomponents. In essence, the device has the form of a skin-adhering patch or bandage.

The present invention provides simple, passive or active, e.g., transdermal, drug delivery apparatuses and methods which are environmentally or medically advantageous.

It is an especially significant aspect of this invention to provide transdermal drug delivery devices having components or subassemblies which can or must be disposed in an environmentally safe, or a therapeutically safe, fashion.

The present invention is, in one aspect, a method of manufacturing a transdermal drug delivery device in which, after usage of the device, a component, a subassembly, or both, are intentionally adapted to be separable from the device, thereby to render the device, the component, or the subassembly more environmentally or medically acceptable. Either the separated component or the structure remaining after separation may be more environmentally or medically acceptable in accordance with this invention.

In a further aspect, the present invention is an electrotransport drug delivery device in which the battery assembly is intentionally adapted to permit batteries therein to be removed therefrom.

In yet a further aspect, the present invention is a transdermal drug delivery device in which the drug reservoirs are intentionally adopted to be detachable from the device and sealable prior to disposal so as to minimize possible contact, e.g., with the skin, between the drug reservoirs and the person disposing of the reservoirs. In one practice of this aspect of the invention, the transdermal device is an electrotransport device and the drug reservoirs are supported by and disposed within a separable, flexible, foldable housing.

The terms "medically acceptable" or "environmentally acceptable" as used herein mean, for example, safely disposable.

In yet a further aspect, an electrotransport drug delivery device of this invention comprises two housings. One of the housings generally contains the electronic components of the system and the other of the housings contains the drug storage components of the system. By means of, e.g., a projection from one of the housings, the two housings are separable from each other and are adapted to permit subcomponents within one or both housings to be separated from the housing for replacement or disposal.

In a preferred practice of this aspect of the invention, the housing containing the electronic components includes a battery connector which permits the battery easily to be detached from the housing and, thereafter, to be separately disposed. In an additional preferred practice of this aspect of the invention, drug reservoirs within the housing containing the drug storage means are adapted to be separable from the housing.

In a most preferred practice of this aspect of the invention, the housing containing the drug storage components is sufficiently flexible to be foldable upon itself, e.g., in half. The housing has cooperating adhesive surfaces which mate to provide a folded configuration. In this manner, exposure of a drug reservoir surface to contact is minimized or prevented. In its folded configuration, the housing containing the drug reservoirs can be handled, e.g., for disposal, without skin or other contact between the drug-containing reservoirs and the person disposing of the housing.

In a preferred aspect, the present invention is directed to a patient-controlled electrotransport drug (e.g., narcotic analgesic) delivery device, especially a patch or bandage-like electrotransport device.

These and other aspects and advantages of the present invention will become apparent from the following detailed description of the invention and from the accompanying drawings.

BRIEF DESCRIPTION OF THE DRAWINGS

In the figures, like parts are given like reference numerals and wherein.

MODES FOR CARRYING OUT THE INVENTION

Generally speaking, the electrotransport device of this invention can be used by patients to deliver substantially any drug during a prescribed course of therapy. One specific example of a course of therapy is the delivery of an analgesic to control pain, e.g., acute postoperative pain. Analgesia is provided when the patient self-administers doses of an analgesic, such as fentanyl, by pressing an on-demand switch on the system. Activation of drug dosage delivery is indicated by visual readout and, preferably, an audible stimulus, e.g., a "beep". The patient is thus able to titrate the drug to his or her pain mitigation needs (within definable limits) to achieve the level of analgesia desired by the patient. The system is compact, portable, self-contained, and is designed to be worn on the patient's skin (e.g., upper arm, lower arm, or chest) for a predetermined period of use. The device will preferably become inoperative at the expiration of a predetermined period of use, e.g., 24 hours. After use, the device can be discarded, returned to the issuing entity, e.g., for replacement, or processed in some other approved manner.

Figure 1:
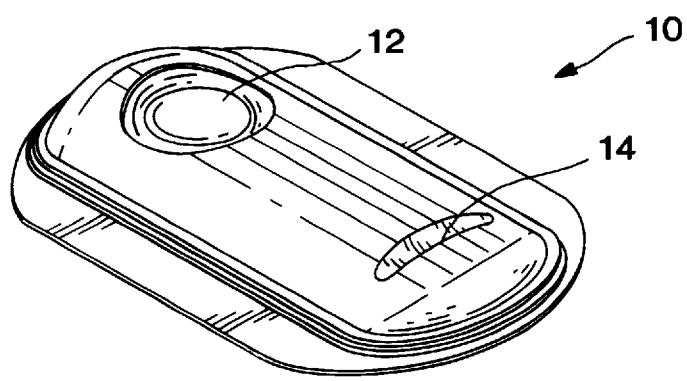
FIG. 1 is a perspective view of an electrotransport device of this invention.

With reference to FIG. 1, there is shown a perspective view of an electrotransport device 10 of this invention. Device 10 comprises an activation means which in this embodiment is a push or dome button switch 12 and a visual readout means or display 14 which in this embodiment is a light emitting diode (LED). In view of the description below, various other structures which operate in a manner similar to that of switch 12 and LED 14 will be suggested to one skilled in this art.

Figure 2:
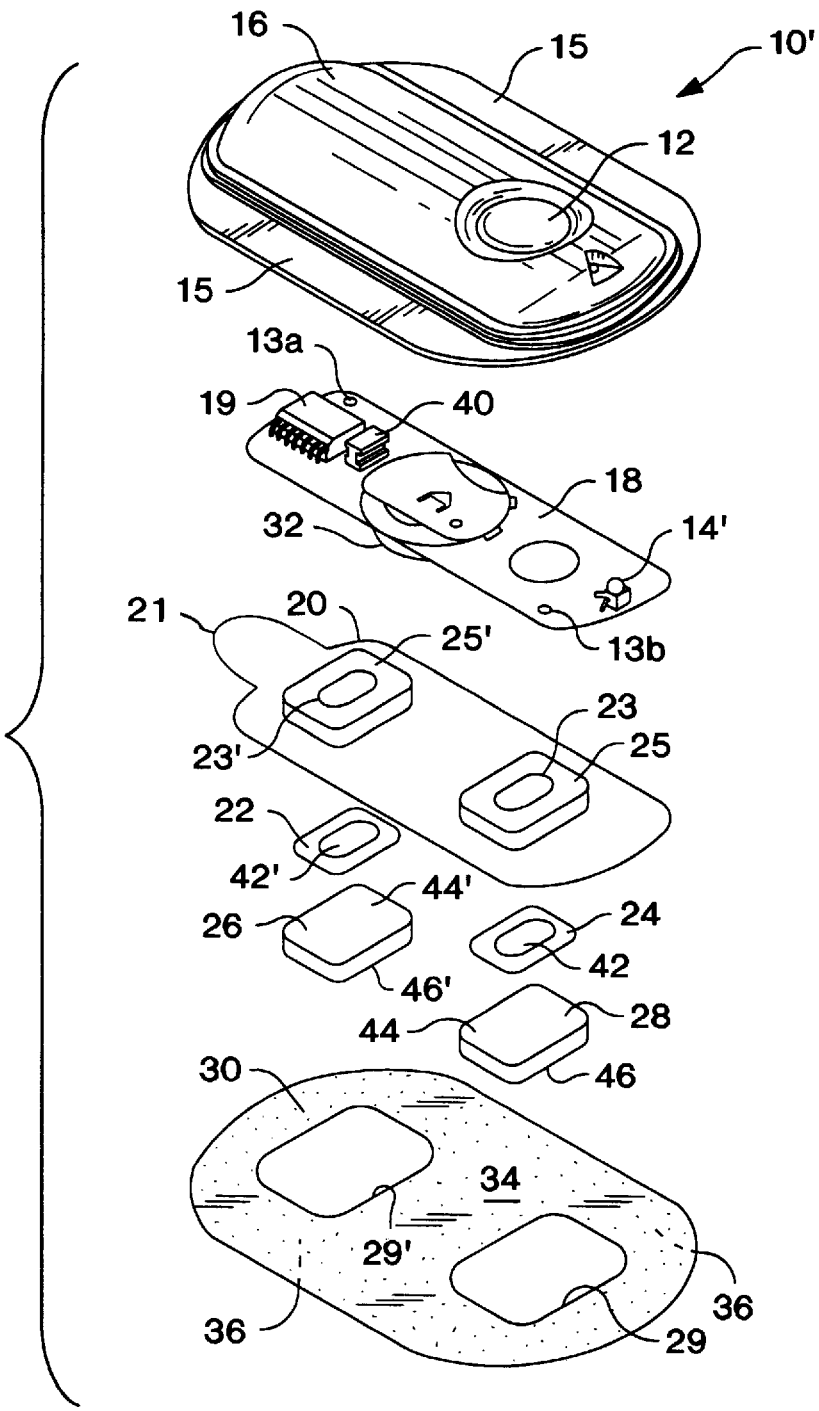
FIG. 2 is an exploded view of a second embodiment of an electrotransport device of this invention.

FIG. 2 is an exploded view of the components of a device 10' similar to that of FIG. 1. Device 10' of FIG. 2 is similar to device 10 of FIG. 1 with the exception that button 12 and LED 14 are located adjacent each other on one end of the device. Device 10' comprises an upper housing 16, a circuit board assembly 18, a lower housing 20, anode electrode 22, cathode electrode 24, anode reservoir 26, cathode reservoir 28 and skin-compatible adhesive 30. Upper housing 16 has lateral wings 15 which assist in holding device 10' upon a patient's skin. Upper housing 16 preferably is composed of a rubber-like, injection moldable material, e.g., ethylene vinyl acetate. The upper housing 16 has two posts, 11a and 11b (best seen in FIG. 4), which extend through openings 13a and 13b in the circuit board assembly 18. The ends of the posts are heated/melted in order to attach assembly 18 to housing 16. Circuit board assembly 18 comprises an integrated circuit 19 electrically coupled to discrete components 40 and to a battery 32. In one aspect of this invention, the extent of securement of circuit board assembly 18 to upper housing 20 is reduced thereby making circuit board assembly 18 separable from housing 20. For example, circuit board assembly 18 may be simply "snapped" onto upper housing 20 by the use of grooved or beaded posts 11a, 11b.

Lower housing 20 has a tab 21 on one end thereof which permits separation of upper housing 16 from lower housing 20. Lower housing 20 is attached to upper housing 16 by means of adhesive 30, the upper surface 34 of adhesive 30 being adhered to both lower housing 20 and upper housing 16, including the bottom (skin side) surfaces of wings 15. Lower housing 20 has wells 23, 23' which are sized to hold electrode assemblies 24, 28 and 22, 26, respectively. Lower housing 20 is preferably composed of an electrically insulating material (e.g., polyethylene) which is substantially impermeable to the passage (e.g., by diffusion) of the drug or other beneficial agent contained in reservoirs 26 or 28.

Partially shown on the underside of circuit board assembly 18 is battery 32. Battery 32 is of the button cell variety. Opposing faces of button cell 32 are of opposite polarity. Polymeric, flexible, and other types of electrochemical cells which are within the design parameters of this system, may be employed.

The device 10' is generally comprised of battery 32, electronic circuitry 19, 40, electrodes 22, 24, and drug/chemical reservoirs 26, 28, all of which are integrated into a self-contained unit. Preferably, the anodic electrode is comprised of silver (e.g., foil or screen) and the cathodic electrode is comprised of silver chloride (e.g., foil or screen). The electrodes 22 and 24 are in direct mechanical and electrical contact with reservoir 26 and reservoir 28, respectively. Both reservoirs 26 and 28 are preferably comprised of polymer hydrogel materials. Electrodes 22, 24 and reservoirs 26, 28 are retained by lower housing 20. The circuit outputs from the electronic circuitry within the circuit board assembly 18 are electrically connected to the electrodes 24 and 22, through the openings in the top of wells 23, 23', by electrically conductive adhesive strips 42 and 42', respectively. Electrodes 22 and 24, in turn, are in direct mechanical and electrical contact with top sides 44', 44 of drug reservoirs 26 and 28. The bottom sides 46', 46 of drug reservoirs 26, 28 contact the patient's skin through the openings 29, 29' in adhesive 30.

Upon depression of push button 12, the electronic circuitry 18 delivers a predetermined DC current to the electrode/reservoirs 22, 26 and 24, 28 for a time period of predetermined length, e.g., about 10 minutes. Agent is delivered through the patient's skin, e.g., on the arm, for the ten minute time period, each ten minute period being a single bolus delivery or drug delivery event. In a preferred practice, the user receives feedback as to the onset of the drug delivery by simultaneous visual (LED 14 becomes lit) and audible signals (the system optionally includes a "beeper" such as a ceramic transducer).

While the invention is not limited to any particular drug, the invention has particular utility in the delivery of analgesics. One particularly suitable analgesic is fentanyl, preferably a hydrochloride or citrate salt of fentanyl. In the case of fentanyl HCl, the anodic reservoir is the "donor" reservoir and contains the fentanyl HCl and the cathodic reservoir contains a biocompatible electrolyte.

The push button switch 12, electronic circuitry on circuit board 18 and battery 32 are encased or sealed within plastic or rubber upper housing 16. Lower housing 20 is preferably composed of a moldable, plastic or elastomeric sheet material which can be easily molded to form depressions 25, 25' with openings 23, 23' therein. Lower housing 20 fits into upper housing 16 and retains drug storage and delivery components 22, 24, 26, and 28. The assembled device 10' is preferably water resistant (i.e., splash proof) and most preferably is waterproof. Device 10' has a low profile that easily conforms to the body thereby allowing freedom of movement at, and around, the wearing site. The anode/fentanyl reservoir (e.g., reservoir 26) and the cathode/salt reservoir (e.g., reservoir 28) are located on the underside of the device 10' and are sufficiently separated to prevent accidental electrical shorting during normal handling and use.

Device 10' adheres to the patient's body surface by means of a peripheral adhesive 30 which has upper and lower adhesive regions 34 and 36, respectively. The lower adhesive region 36 has adhesive properties which assures that the system remains in place on the body (e.g., the skin) during normal user activity, and yet permits reasonable removal after the predetermined (e.g., 24-hour) wear period. Upper adhesive 34 adheres to lower housing 20 and to upper housing 16, thereby joining and sealing upper and lower housings 16, 20 together.

The switch 12 may be easily located and actuated through clothing. A double press within a short time period, e.g., three seconds, is used to activate the 10 minute delivery period while still minimizing the likelihood of inadvertent actuation of the device 10'.

Figure 3:
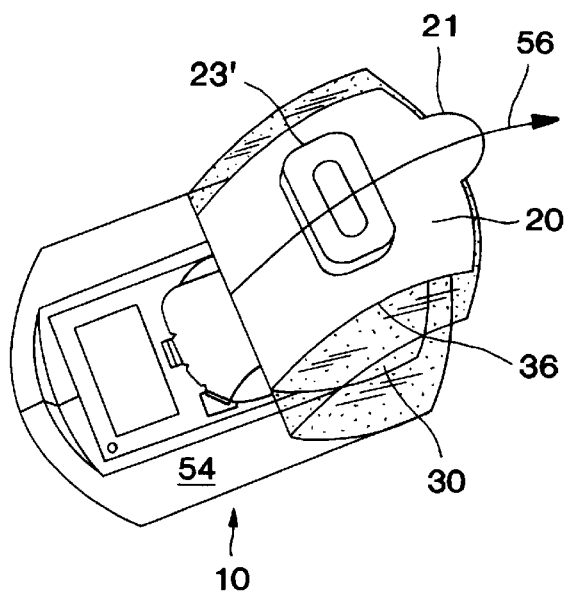
FIG. 3 illustrates the steps for removing and separately discarding the drug reservoir of a device of this invention.
Figure 3:
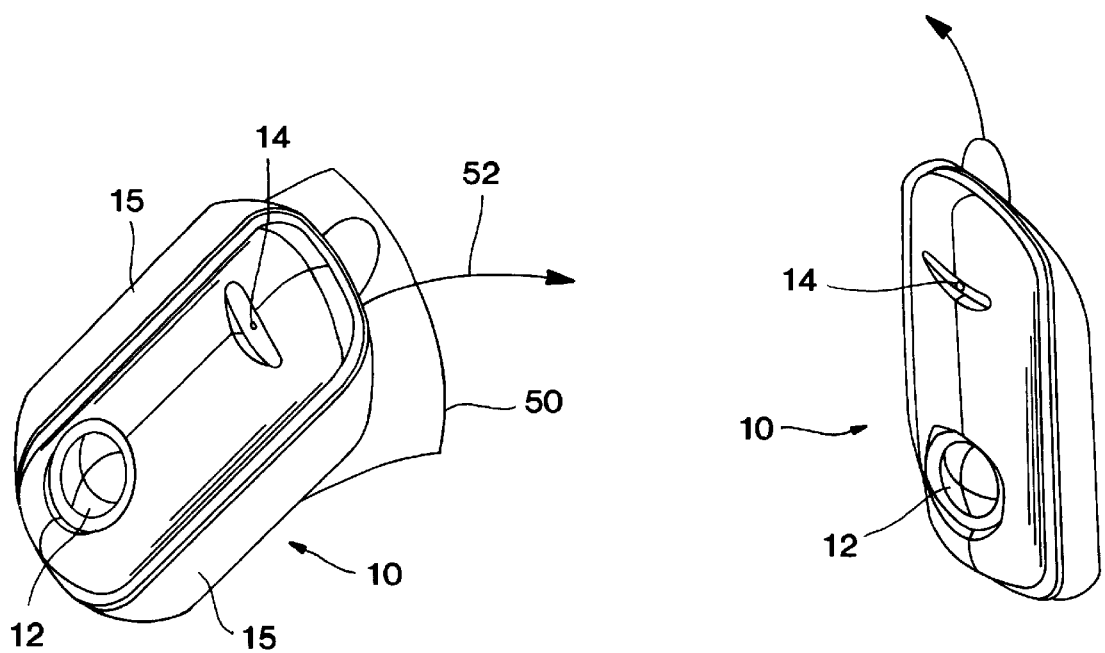

In FIG. 3, there is shown, starting in the lower lefthand corner and proceeding counterclockwise therefrom, a device 10, as it appears after removal from protective packaging (not shown). Device 10 has a substantially rectangular release liner 50 covering the skin contact adhesive 30. Release liner 50 covers and protects adhesive 30 as well as any adhesive on the underside of wings 15. Arrow 52 indicates the direction in which release liner 50 is peeled from the bottom of device 10 before applying the device on the skin of a patient.

In the lower righthand corner of FIG. 3 there is shown a device substantially as it appears when vertically disposed on, for example, the arm or upper body of a patient using the device. For purposes of clarity, no patient is shown in FIG. 3. Push button 12 is used to activate the device with LED 14 being lit during the drug delivery interval.

In the upper righthand corner of FIG. 3 there is shown the underside 54 of device 10. Arrow 56 shows the direction of peel of tab 21 located on lower housing 20. Lower housing 20 contains electrodes 22, 24 and drug reservoirs 26, 28. As is shown, lower housing 20 is sufficiently flexible so as to be peeled from the upper housing and to be folded back upon itself. Lower housing 20 has adhesive 30 covering the under surface (i.e., on the skin side) thereof. Lower adhesive region 36 provides the means by which lower housing 20 may be folded back upon, and adhered to, itself, thereby retaining drug reservoirs 26, 28 (and electrodes 22, 24) therein. (A folded lower housing 20 is better shown in FIG. 4 described below.) In the folded configuration, the drug impermeable portions of housing 20 are exposed to handling. In this manner, the entirety of lower housing 20 with any residual drug in the drug reservoir safely contained therein can be safely sealed and, if desired, discarded. At a minimum, opportunities for skin contact between materials (e.g., drugs) in reservoir 26 and/or 28 within lower housing 20 and the user of device 10 are minimized.

Figure 4:
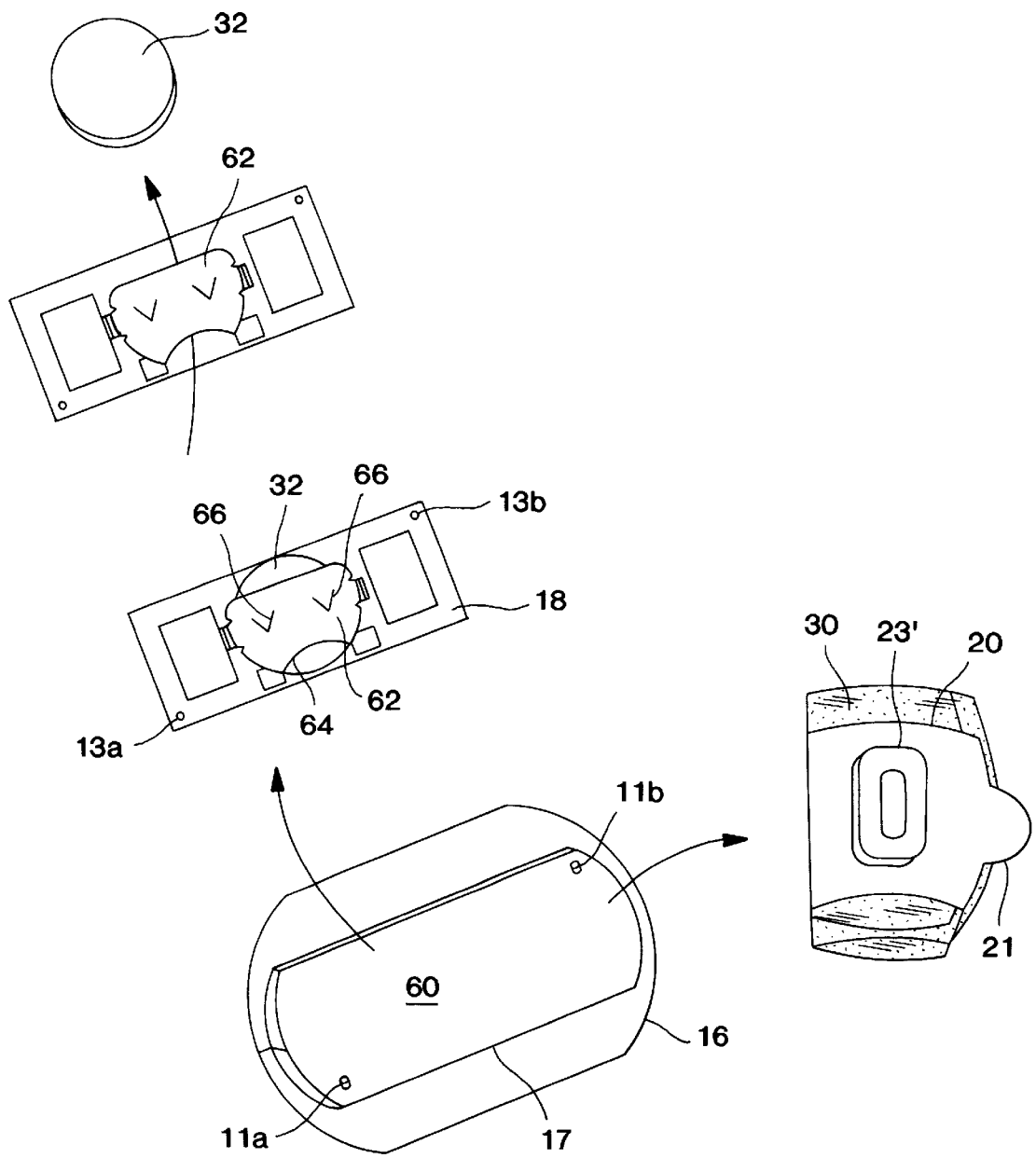
FIG. 4 illustrates the steps for removing and separately discarding the battery of a device of this invention.

FIG. 4 illustrates a further aspect of the present invention in which battery 32 is removed from circuit board assembly 18 and is discarded, preferably in an environmentally acceptable manner.

In this embodiment of the invention, the battery contact structure has been intentionally designed to permit ease of battery separation from its contact structure. For example, battery 32 may simply be slid from its connector. Various other approaches will be readily apparent to one skilled in this art in view of this disclosure.

Starting at the bottom in FIG. 4, there is shown the underside 60 of upper housing 16. Upper housing 16 normally contains therein the circuit board assembly 18. The circuit assembly 18 lifts out of the depression 17 (i.e., by tearing the heat staked portions of housing 16) after the lower housing 20 has been peeled off as described earlier herein. The circuit board assembly 18 comprises battery connector housing 62. Battery connector housing 62 includes an arcuate slot 64 and tabs 66 which are bent inwardly from the outside plane of housing 62 so as to achieve contact with one pole of battery 32. The opposite pole of battery 32 is, of course, its opposite face which is not shown in FIG. 4. Thus, battery connector 62 provides the electrical contact between battery 32 and circuit assembly 18. As is shown, circuit board assembly 18 is heat stacked into upper housing 60 and can be completely removed therefrom by tearing the heat stakes through openings 13a and 13b in assembly 18. Battery connector 62 is intentionally designed so that battery 32 may be removed from connector 62 as is shown in the upper left of FIG. 4. For example, battery 32 may be manually removed by sliding battery 32 out from connector 62 and separated from circuit board assembly 18. This is shown in the upper left of FIG. 4. It will be appreciated that removal of circuit board assembly 18 from upper housing 60 is one potential application of the present invention. Circuit board assembly 18 may contain environmentally hazardous or otherwise objectionable components which necessitate its controlled disposal after separation from the other components of the device. It is to be further understood that battery 32 may be the only component that is specifically designed to be removed from the partially disassembled device. Components containing expensive raw materials may be similarly designed in accordance with this invention.

Once removed from circuit board assembly 18, battery 32 may be disposed in accordance with local environmental policies. Thus, the present invention permits an increased or an enhanced environmental compliance by intentionally providing the structure whereby environmentally impacting structures such as batteries, electronic circuitry or potentially medically injurious structures such as drug reservoirs may be removed or detached from the drug device assembly itself.

In light of the above disclosure, there are likely to be numerous variations and alternatives to the presently-described method and structure which will occur to one skilled in this art. All such structures, variations, and alternatives are to be included within the scope of the attached claims.

What is claimed is:

1. A method of discarding drug-containing portions of a transdermal electrotransport drug delivery device, the device including an electrical power source, a pair of electrodes electrically connected to the power source and a drug reservoir in electrical contact with one of said electrodes, the drug reservoir being positioned in a housing which is separable from the device, the housing having an adhesive surface, the housing being foldable upon said adhesive surface when the housing is separated from the device, comprising:

separating the housing containing the drug reservoir from the device; and folding the separated housing upon itself to adhesively seal the drug reservoir within the folded housing.

2. The method of claim 1, further including separating the housing from the device by pulling a tab located on the housing.

3. The method of claim 1, further including a counter electrode reservoir in the housing.

4. The method of claim 1, further including a donor electrode and the associated drug reservoir in a first part of the housing, and a counter electrode and an associated electrolyte reservoir in a second part of the housing.

5. The method of claim 4, wherein the housing is folded between the first and second parts.

6. The method of claim 5, wherein the drug reservoir and the electrolyte reservoir are brought into face-to-face contact after said folding.

7. The method of claim 1, including operating the device with the housing in place to deliver drug transdermally from the drug reservoir to a patient via electrotransport and thereafter performing said separating step.

8. The method of claim 7, wherein the adhesive contacts the patient during the electrotransport drug delivery.

9. The method of claim 1, wherein the housing is comprised of a polymer.

10. The method of claim 9, wherein the polymer is substantially impermeable to the passage of the drug.

11. The method of claim 9, wherein polymer comprises polyethylene.

12. The method of claim 1, wherein the folded housing is discarded separately from the remaining portions of the device.

13. The method of claim 1, wherein the folded housing allows the drug reservoir to be discarded with minimal contact with the drug reservoir.

14. The method of claim 1, wherein the device includes an electrical circuit having a pair of circuit outputs, the electrical circuit controlling electrotransport current applied by the device, a pair of electrodes electrically connected to the circuit outputs and a drug reservoir in electrical contact with one of said electrodes, the electrical circuit being on a substrate positioned in a device housing, the substrate being secured to the housing by means of a manually tearable connection, further comprising:

tearing the connections by pulling the substrate from the housing; and separately discarding the substrate from the remaining portions of the device.

15. The method of claim 14, wherein the substrate comprises a board.

16. The method of claim 14, wherein the manually tearable connection comprises a polymeric stake passing through the substrate, the end of the stake being melted to secure the substrate on the stake.

17. The method of claim 16, wherein the manually tearable connection comprises a plurality of said polymeric stakes.

18. The method of claim 14, wherein the electrical circuit includes a battery.

19. The method of claim 18, further including separating the battery from the electrical circuit after the tearing and pulling step and disposing the battery separately from the electrical circuit.

* * * * *